United States Patent [19]

Randolph

[11] Patent Number: 5,124,265
[45] Date of Patent: Jun. 23, 1992

[54] METHOD AND APPARATUS FOR CRYSTALLIZATION PROCESS CONTROL

[75] Inventor: Alan D. Randolph, Tucson, Ariz.

[73] Assignee: Arizona Technology Development Corporation, Tucson, Ariz.

[21] Appl. No.: 601,930

[22] Filed: Oct. 15, 1990

[51] Int. Cl.$^5$ .......................... G01N 15/02; B01D 9/00
[52] U.S. Cl. .......................................... 436/55; 436/4; 422/245; 422/252; 422/110
[58] Field of Search ............................ 422/245, 252, 110; 423/DIG. 5; 436/4, 55

[56] References Cited

U.S. PATENT DOCUMENTS

| | | | |
|---|---|---|---|
| 4,025,307 | 5/1977 | Randolph et al. | 23/230 |
| 4,260,010 | 4/1981 | Randolph | 422/245 |
| 4,263,010 | 4/1981 | Randolph | 23/230 |
| 4,294,807 | 10/1981 | Randolph | 423/242 |
| 4,395,493 | 7/1983 | Zahniser et al. | 435/808 |
| 4,512,954 | 4/1985 | Matsui | 422/110 |

*Primary Examiner*—David L. Lacey
*Assistant Examiner*—David Redding
*Attorney, Agent, or Firm*—Antonio R. Durando; Harry M. Weiss

[57] ABSTRACT

A crystallizer control method and apparatus that generate control signals to manipulated process parameters on the basis of on-line information derived from the measurement of the crystal population in a selected size range in the crystallizer slurry. According to one embodiment of the invention, a particle counter probe is immersed directly into the fines removal circuit of the crystallizer for on-line measurement of crystal population in the 16 to 32 micron size range. The data so collected are then used directly in a standard proportional controller apparatus to manipulate certain operating parameters, such as fines removal rate and feed rate, to effect the desired result. Applying this model-independent control method to a KCl crystallizer, the steady-state conditions of the crystal size distributions were reestablished after an upset in approximately half the time required when no control was applied. The maximum perturbation of the performance index in the controlled case was approximately 65 percent of the magnitude registered without control. The perturbation of the crystal population in the 16-32 micron range was approximately half of that seen without control.

15 Claims, 1 Drawing Sheet

METHOD AND APPARATUS FOR CRYSTALLIZATION PROCESS CONTROL

BACKGROUND OF THE INVENTION

1. Field of the Invention

This invention pertains to the general field of process dynamics modeling and control. In particular, it relates to a new and improved method and apparatus for on-line control of continuous crystallizers in order to optimize the operating response to perturbations from steady-state.

2. Description of the Prior Art

Mathematical modeling of the dynamic behavior of process parameters is the basic tool of process control. Once a mathematical relationship between measurable parameters is established either empirically or on the basis of the physics and chemistry of the process, intelligent choices can be made to manipulate certain process parameters in order to control others. Control theory and technology provide the necessary procedure and hardware to accomplish desired goals in an optimal way.

In the case of crystallization and related equipment, maximization of the production of crystals of a desired size distribution is the most important process control objective. Since industrial crystallizers operate at steady state under predetermined target conditions proven experimentally to be optimal for a given process, it is very important to be able to maintain such steady-state conditions and to minimize the effect of any perturbation on the rate of production and size distribution of the crystal product. To that end, much research has been devoted toward finding crystallization models and control procedures that are practical for on-line implementation.

Investigators have shown that the crystal size distribution in crystallizers depends on the kinetics of crystal nucleation and growth, as well as on the constraints and geometry of the equipment. In the case of steady state operation of continuous mixed-suspension type of crystallizers, which are widely used in industry and in the laboratory, it has been found that the population density of each crystal size is represented by the relationship $$n(L) = n^0 \exp(-L/GT),$$

where $n(L)$ is the number of crystals o linear size L per volume of product slurry in a size range $\Delta L$ (population density), G is the crystal linear growth rate, T is the crystallizer's holding time, and $n^0$ is the population density of embryonic crystals (nuclei) of size vanishingly close to zero. In terms of the cumulative members, $N(L)$, of the crystal population distribution per volume of product slurry, the population density $n(L)$ is defined as the limit of the ratio $\Delta N(L)/\Delta L$ as $\Delta L$ tends to zero. A complete derivation of the relationship given above appears in Chapter 4 of "Theory of Particulate Processes," Alan D. Randolph et al., Academic Press, New York, Second Edition, 1988.

The exponential form of this steady-state model has been valuable in providing a tool for easy calculation of important but otherwise unmeasurable quantities, such as the nuclei population density n° and the growth rate G. By plotting on semi-logarithmic paper the population density $n(L)$ as a function of particle size L, which in practice can be measured with accuracy for all except the most minute sizes (of the order of units of microns), a straight line results, and $n^0$ and $1/GT$ can be derived from its intercept and slope, respectively. Since the holding time for a mixed-product-removal crystallizer is equal to the ratio of the crystallizer's volume and the slurry withdrawal rate, the growth rate G can be calculated from the slope of that line. Similarly, the nucleation rate for the system $B^0$, defined as the product of the nuclei population density $n^0$ and the growth rate G, can be calculated from the information so derived. Once these parameters are determined for a given process and the related equipment, control theory provides the necessary algorithms based on the corresponding model to effect process behavior by manipulating predetermined operating parameters that best suit the practical needs and limitations of the crystallizer at hand.

The model given above has been confirmed by much experimental data demonstrating the inverse exponential functionality of $n(L)$ versus L. Therefore, for a given crystallizer operating at steady state with given nuclei population density, growth rate and holding time, it has been shown that the number of crystal particles found in any size interval $\Delta L$ decreases exponentially as L increases. In a practical sense, this means that most particles in the crystallizer are smaller than the cut-off size of the product, which is purposely chosen large for quality considerations. Since crystal growth results from mass transport of solute at the surface of existing crystals, product yield (that is, the crystal mass corresponding to the fraction of the crystal population larger than the cut-off size) can be improved by reducing the number of fine particles in the crystallizer, so that the solute is more likely to be transported and contribute to the growth of product-size particles. Thus, a fines removal system is commonly included in continuous crystallizer operation and it is recognized practice to adjust (optimize) the classification and removal of fines in order to enhance crystal growth in the product size-range. When present, an overflow removal circuit serves the same purpose and, in addition, it allows a heavier slurry density to exist in the crystallizer.

Notwithstanding this typical particle size distribution, most of the mass in the product slurry (underflow) is found within crystals larger than the cut-off size because of the cubic relationship between the mass of a particle and its linear dimension. For example, a typical industrial crystallizer producing potassium chloride, operating at steady state with a product cut-off size of 150 to 200 microns, will produce a particle size distribution containing approximately 70 percent of the crystal population below the product cut-off range and 70 percent of the crystal mass above it.

The above described model has been used to calculate crystallization parameters and understand the mechanisms of crystal growth in a variety of applications. For instance, in U.S. Pat. No. 4,025,307 (1977), Randolph et al. use the characteristics of the model to determine the stone-forming crystallization properties of urine from individual patients. From a more precise definition of the kinetics of formation and growth of crystals from urine and the effect of potential inhibitors, a tool is made available for controlling the incidence and proliferation of kidney stones.

In a totally different application, U.S. Pat. No. 4,294,807 to Randolph (1981) teaches the use of the same model in a system for removing flue gas desulfurization solids using a lime or limestone slurry scrubbing solution. Through a better understanding of the mechanisms of particle growth derived from the model, a system is provided to increase the particle size and modify the crystal habit in order to aid the filtration of the process solids and improve the quality of the waste product.

Because of the much greater population density of fine particles mentioned above, it follows that from a practical point of view sufficient information to fit and apply the above described model can be gathered by analyzing samples containing fines only (that is, particles in the size range below the product cut-off size) and neglecting the product population density. In U.S. Pat. No. 4,263,010 (1981), Randolph uses this principle to control the steady-state operation of a continuous crystallizer. By sampling the fines removal circuit only, this patent teaches that an accurate semi-log population density versus size plot can be constructed so long as the data are derived from a sequence of size intervals containing at least three percent of the total crystal mass of fines in the crystallizer. Therefore, the model is derived by on-line measurements of a preconditioned, classified sample of the population distribution with a zone sensing or light scattering particle analyzer. A computerized control apparatus selects a sufficiently large fraction from the resulting population density data and applies regression techniques to fit the model and calculate the nuclei population density and growth rate. This information is in turn used to generate control signals to various manipulated control parameters to maintain process conditions or reduce the effect of perturbations to the steady state. This patent is closely related to the present invention, which is an improvement thereof, and is therefore incorporated herein by reference for the purpose of more fully describing the scope of application of this invention.

It is apparent from the foregoing that the control techniques in the prior art have required sophisticated manipulation of the population density data to fit a specific mathematical model. In addition, the quality of the resulting control depends on how suitable that model is for the specific process being simulated. Therefore, it would be very desirable to develop a model-independent method for crystallizer process control, especially if it comprised a simplification of the computational requirements for the apparatus. The present invention addresses this need and utilizes a novel approach to the use of crystal population information for process control purposes.

SUMMARY OF THE INVENTION

One of the objectives of this invention is the development of an on-line control method and apparatus for maintaining steady-state operating conditions and for reducing the response time to eliminate changes caused by process perturbations. This is achieved by a novel approach based on the discovery of a direct correlation between the population of fines in some small size range and the crystal nucleation rate.

Another objective of the invention is a control method of general applicability to different crystallization processes and equipment. This is accomplished by the use of a control algorithm that is model independent and utilizes data directly from on-line measurements of crystal population, without the necessity of first fitting a predetermined mathematical model.

Finally, an objective of this invention is the realization of the above mentioned goals in an economical and commercially viable manner. This is done by utilizing apparatus components that are either already available in the open market or can be manufactured at competitive prices.

According to the foregoing objectives, this invention describes a crystallizer control method and apparatus that generate control signals to manipulated process parameters on the basis of on-line information derived from the measurement of the crystal population in a selected size range in the crystallizer slurry. According to one embodiment of the invention, a particle counter probe is immersed directly into the fines removal circuit or the body of the crystallizer for on-line measurement of crystal population in a predetermined, significant size range. The data so collected are then used directly in a standard proportional controller apparatus to manipulate certain operating parameters, such as fines removal rate and feed addition rate, to effect the desired result.

Various other purposes and advantages of this invention will become clear from its description in the specifications that follow, and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

The heart of this invention lies in the discovery that the total number of crystals within some small size range found in a given volume of slurry in a mixed-suspension crystallizer is, by itself, a good measure of the nucleation rate for that system and can, therefore, be used directly as a process control variable. Accordingly, the control techniques described in the Randolph '010 Patent, referenced above, can be implemented and equivalent results can be achieved with simpler apparatus and without fitting the measured data to any particular model.

Specifically, while the teachings of the prior art required the determination of the nucleation rate $B^0$ through a sequence of calculations based on sample readings of n(L) as a function of L, and then required the corresponding fitting of the data to the population density model discussed above in order to provide inputs to the control algorithm, the method and apparatus of this invention provide such inputs directly from readings of just particle members over a narrow predetermined size range.

Figure 1:
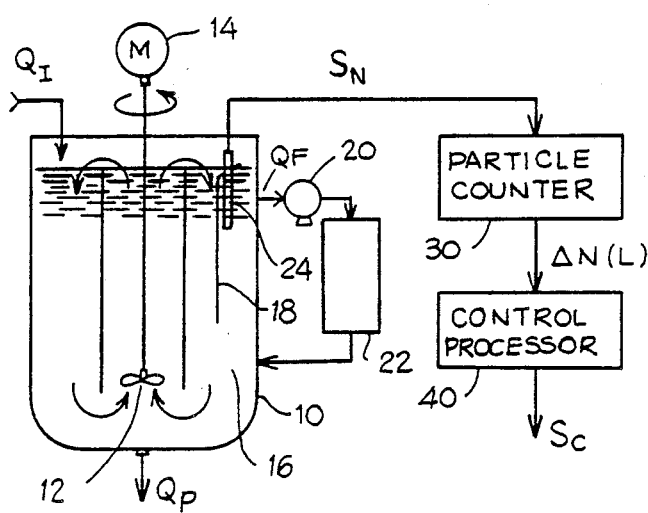
FIG. 1 is a schematic diagram of a crystallizer equipped with control apparatus according to this invention.

Referring now to the drawings, wherein like parts are designated throughout with like numerals, FIG. 1 shows a simplified schematic representation of a typical mixed-suspension crystallizer equipped with one embodiment of the control apparatus of this invention.

A crystallizer vessel 10 is provided where a supersaturated solution is continuously fed at an input rate $Q_i$ for crystal nucleation and growth. The supersaturated mother liquor is stirred by a standard agitator 12 driven by a variable speed motor 14 in order to create a well mixed suspension within the entire body of the crystallizer, except for the area 16 defined by an adjustable baffle 18 to form a classifier for the removal of fines from the vessel 10 at a rate $Q_F$. These fines are withdrawn by a pump 20, dissolved in a dissolver 22, and the resulting supersaturated solution is recycled to the crystallizer. A product slurry (underflow) is continuously withdrawn from the bottom portion of the unit at a rate $Q_P$. An overflow circuit, not shown in the drawings, is used in double draw-off crystallizers to effect the preferential removal of crystals below the cut-off size, hence independently adjusting the slurry density.

According to the specific teachings of this invention, a particle population reading within a narrow size range is taken continuously through the probe 24 of a particle analyzer positioned either in the fines withdrawal region or in the main body of the crystallizer. Although the location of the probe is not critical to the invention, it may be convenient to place it in the fines removal area of the crystallizer in order to minimize interference by product crystals, which are much larger than the size range of interest for control purposes. Depending on the kind of equipment used, it may be necessary to take a sample stream from the crystallizer and route it through the particle analyzer, as illustrated in prior art patents, instead of collecting the data directly from the probe. In the preferred embodiment described here, the particle analyzer marketed by Laser Sensor Technology, Inc. under the trademark "Par-Tec" was used, but any particle counter capable of reliably monitoring crystal population in real time would be acceptable.

The count signal $S_N$ collected by the probe 24 is processed by the particle counter 30 for the determination of the crystal population within the selected particle size interval. This population information $\Delta N(L)$ is then fed to a control processor 40 that calculates and emits a control signal $S_c$ according to predetermined control criteria. As described in the Randolph's '010 Patent, the control signal $S_c$ can be directed to a variety of manipulated variables in various embodiments of on-line control apparatus, all of which are well understood by those skilled in the art. Therefore, the details of the many control algorithms and types of hardware that can be used to implement the method of this invention are not described here. Reference is made to that patent and to Chapter 8 of "Theory of Particulate Processes," cited above, for a general description of control theory as applied to crystallization systems. By way of example, the use of a simple proportional controller in a KCl crystallizer is illustrated here.

Figure 2:
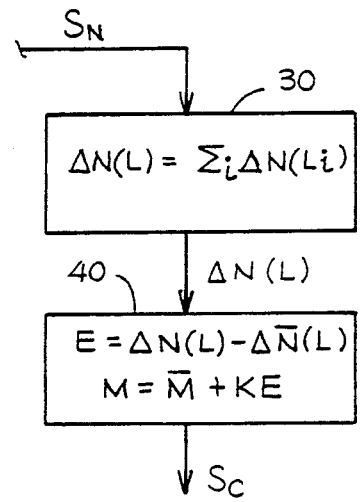
FIG. 2 is a schematic representation of the particle analyzer and the control processor according to one embodiment of the invention.

Referring to FIG. 2, a schematic representation of the particle counter 30 and the control processor 40 according to this embodiment of the invention is shown. The probe 24 of the Par-tec analyzer transmits on-line signals $S_N$ to its processing unit 30 to determine the number of particles $\Delta N(L_i)$ present in each discrete size range i represented by the average size $L_i$ corresponding to a particle counter channel. Thus, a sufficiently wide range of particle size $\Delta L$, represented by a sequence of average sizes $L_i$ measured by corresponding particle analyzer channels, is chosen for particle population measurements. The range between 16 and 32 microns was chosen for the example reported here and similarly narrow ranges have proven sufficient for controlling steady-state crystallization in general, so long as at least 15 percent of the crystal population is contained in the selected size range. The particle count $\Delta N(L)$ in the selected range is transmitted to the control processor 40 which compares it to its value $\Delta N(L)$ at steady state and calculates the change E. The processor then calculates a new set-point value for the chosen manipulated variable M on the basis of elementary proportional control theory and emits a control signal $S_s$ for use by the appropriate control apparatus (not shown in the drawings). The preferred manipulated variables for practicing this invention include the fines removal rate, the supersaturated solution feed rate, the product cut-off size, and the overflow to underflow ratio (when an overflow circuit is present in the crystallizer).

Any particle analyzer normally used for this type of application is suitable for practicing the invention. A light scattering particle analyzer of the type available from the Leeds and Northrup Company under the trademark "Microtrac" can be used, but it would be desirable to convert the resulting weight fraction measurements (this instrument first measures particle counts and it internally computes weights) to population density and crystal count values by simple computations, as illustrated in the referenced prior art. If an electrical zone sensing particle analyzer is used, such as the "Coulter" counter manufactured by Coulter Electronics, the population values for each selected size $L_i$ are directly available.

EXAMPLE

The effective use of on-line measurements of crystal population within the 16–32 micron range to control the operation of steadystate crystallization was demonstrated with a KCl crystallizer of the type shown in FIG. 1. After steady state was reached at 100 F with a feed rate of 300 ml/min, a fines removal rate of 750 ml/min and a product withdrawal of 300 ml/min, a major upset was introduced by mixing acetone in the supersaturated mother liquor. Acetone is known to cause a burst of nuclei of KCl crystals under these conditions. The resulting changes in particle size over the entire crystal population were measured and quantified in terms of the following performance index:

$$PI = [\ N(L_i)/\_N(L_i) - 1]^2,$$

where i corresponds to each of the six measurement channels available in the Par-tec equipment. Parallel runs were performed, with no control and with proportional control. The selected manipulated variable was the fines removal rate $Q_F$, controlled with a delayed signal based on the residence time of the fines, as illustrated in the Randolph '010 Patent, and on a proportional controller gain of 0.125.

Figure 3:
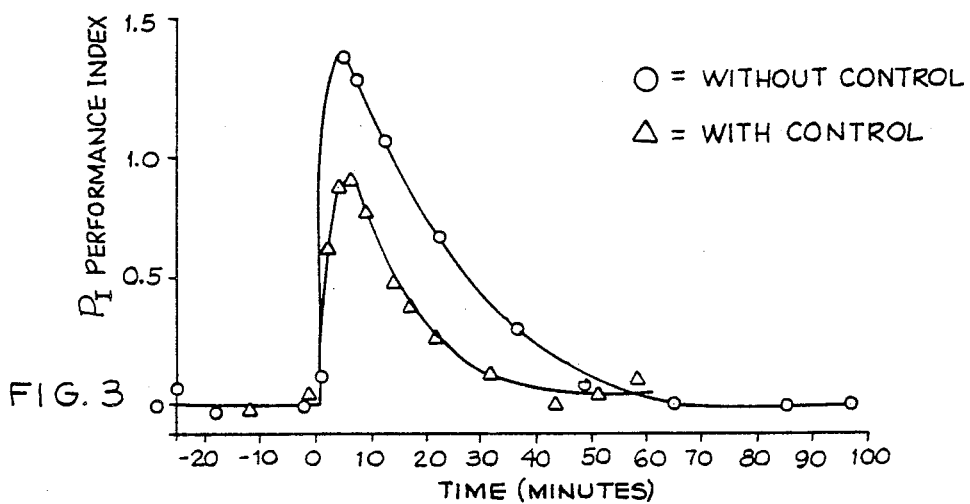
FIG. 3 shows the dynamic response of a crystallizer, with and without control according to this invention, over a period of 60 minutes following an upset to steady-state conditions.
Figure 4:
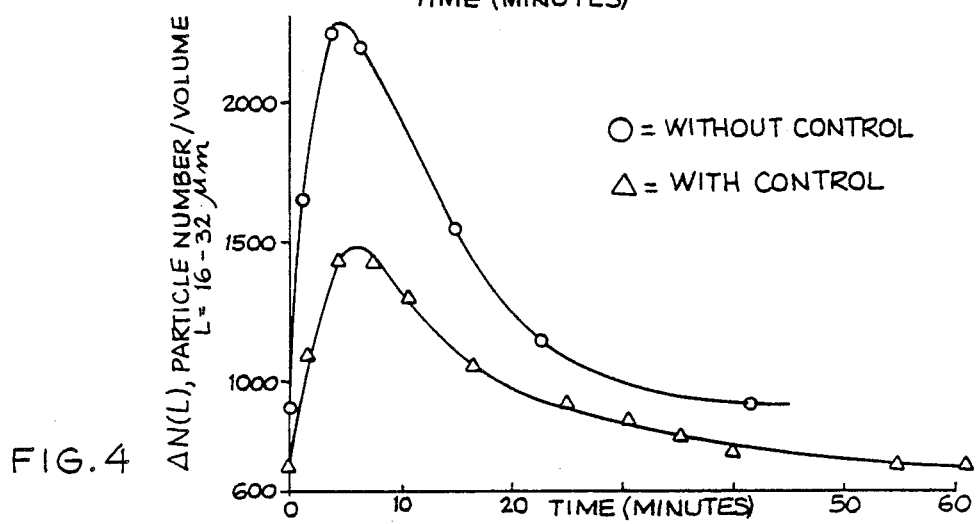
FIG. 4 shows the changes in crystal population, with and without control according to this invention, measured within a 16 to 32 micron window.

FIG. 3 shows the dynamic response of the crystallizer, as measured by the performance index described above, over a period of 60 minutes following the upset to the steady-state operation. FIG. 4 shows the corresponding changes in crystal population within the selected 16 to 32 micron window analyzed by the Par-tec counter. As apparent from these graphs, the model-independent control method of this invention, based simply on particle counts, was able to reestablish steady-state conditions of the crystal size distribution after an upset in approximately half the time required when no control was applied. The maximum perturbation of the performance index in the controlled case was approximately 65 percent of the magnitude registered without control. Similarly, the perturbation of the crystal population in the 16-32 micron range was approximately half of that seen without control.

These results are comparable to those obtained with prior art methods of control. Thus, this invention teaches a new and useful method of control that permits the on-line control of crystallizer operating parameters to maintain steady state on the basis of a model-independent control algorithm, where the input to the algorithm is simply the measured variable consisting of the crystal population in a narrow size range.

Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What I claim is:

1. A combination of an apparatus for the on-line model-independent control of a steady-state crystallization process in a mixed-suspension crystallizer by the manipulation of process parameters in response to perturbations in the crystal population, said apparatus comprises:
   (a) means for determining the crystal population in the crystallizer in a selected range of particle sizes containing at least 15 percent of the total crystal population, said means having a probe for positioning anywhere within the crystallizer; and
   (b) means for developing a model-independent signal, in direct response to perturbations in said crystal population, for controlling at least one manipulated process parameter selected from the group consisting of the fines removal rate from the crystallizer, the feed rate of supersaturated solution to the crystallizer, the fines cut-off size in the classifier portion of the crystallizer, and the overflow to underflow ratio in the crystallizer, wherein said manipulated process parameter is adjusted in real time to maintain steady-state operating conditions.

2. The apparatus described in claim 1, wherein said means for determining the crystal population in said crystallizer comprises:
   a laser probe means for immersion in the fines removal section of the crystallizer for the direct development of a crystal count signal; and
   a particle counter means for the real time conversion of the crystal count signal so developed into a crystal population value for said selected range of particle sizes for transmission to said means for developing a signal for controlling at least one manipulated process parameter in response to perturbations in said crystal population.

3. The apparatus described in claim 1, wherein said means for developing a signal for controlling at least one manipulated process parameter in response to perturbations in said crystal population consists of a proportional controller.

4. The apparatus described in claim 3, wherein said means for developing provides a signal for controlling the fines removal rate from the crystallizer.

5. The apparatus described in claim 3, wherein said means for developing provides a signal for controlling the feed rate of supersaturated solution to the crystallizer.

6. The apparatus described in claim 3, wherein said means for developing provides a signal for controlling the fines cut-off size in the classifier portion of the crystallizer.

7. The apparatus described in claim 3, wherein said means for developing provides a signal for controlling the overflow to underflow ratio in the crystallizer.

8. A model-independent method for controlling a steady-state crystallization process in a mixed-suspension crystallizer by the on-line manipulation of process parameters in response to perturbations in the crystal population, which comprises the following steps:
   (a) determining the crystal population in the crystallizer in a selected range of particle sizes containing at least 15 percent of the total crystal population; and
   (b) developing a model-independent signal for controlling at least one manipulated process parameter, selected from the group consisting of the fines removal rate from the crystallizer, the feed rate of supersaturated solution to the crystallizer, the fines cut-off size in the classifier portion of the crystallizer, and the overflow to underflow ratio in the crystallizer, in response to perturbations in said crystal population in a selected range of particle sizes, wherein said process parameter is adjusted in real time to maintain steady-state operating conditions.

9. The method described in claim 8, wherein said selected range of particle sizes containing at least 15 percent of the total crystal population includes all crystal sizes between approximately 16 and 32 microns.

10. The method described in claim 9, wherein a proportional controller performs the step of developing a control signal to at least one manipulated process parameter in response to perturbations in the crystal population contained in said 16 to 32 micron size range.

11. The method described in claim 10, wherein said manipulated process parameter adjusted in real time to maintain steady-state operating conditions consists of the fines removal rate from the crystallizer.

12. The method described in claim 10, wherein said manipulated process parameter adjusted in real time to maintain steady-state operating conditions consists of the feed rate of supersaturated solution to the crystallizer.

13. The method described in claim 10, wherein said manipulated process parameter adjusted in real time to maintain steady-state operating conditions consists of the fines cut-off size in the classifier portion of the crystallizer.

14. The method described in claim 10, wherein said manipulated process parameter adjusted in real time to maintain steady-state operating conditions consists of the overflow to underflow ratio in the crystallizer.

15. The method described in claim 11, wherein the step of determining the crystal population in the crystallizer consists of providing a laser probe means immersed in the fines removal section of the crystallizer for the direct development of a crystal count signal, and providing a particle counter for the real time conversion of the crystal count signal so developed. into a crystal population value for said selected range of particle sizes for developing a control signal to at least one manipulated process parameter in response to perturbations in said crystal population.

* * * * *